United States Patent [19]

Ohmori et al.

[11] Patent Number: 5,135,952
[45] Date of Patent: Aug. 4, 1992

[54] ANTIINFLAMMATORY AND/OR ANTIALLERGIC METHODS

[75] Inventors: Shinji Ohmori, Okayama; Kazumi Ogata, Toyonaka; Takahiro Sakaue, Itami, all of Japan

[73] Assignee: Senju Pharmaceutical Co., ltd., Osaka, Japan

[21] Appl. No.: 550,366

[22] Filed: Jul. 10, 1990

[30] Foreign Application Priority Data

Jul. 14, 1989 [JP] Japan .................... 1-183484

[51] Int. Cl.$^5$ .................. A61K 31/195; A61K 31/225
[52] U.S. Cl. .................... 514/547; 514/562; 514/825; 514/885
[58] Field of Search ................ 514/547, 562

[56] References Cited

U.S. PATENT DOCUMENTS 4,102,995  7/1978  Hebborn ........................ 424/81
4,755,535  7/1988  Minaskianian et al. ........ 514/947

FOREIGN PATENT DOCUMENTS 306192  3/1989  European Pat. Off. .
63-8337  1/1988  Japan .
1-79956  3/1989  Japan .

OTHER PUBLICATIONS

Chemical Abstracts 113:21252a (1990).

Primary Examiner—Leonard Schenkman
Attorney, Agent, or Firm—Wenderoth, Lind & Ponack

[57] ABSTRACT

The present invention relates to a useful antiinflammatory and/or antiallergic composition comprising a compound of the formula:

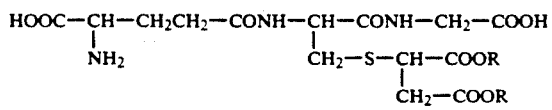

(wherein the R's are same or different and each means a hydrogen atom or lower alkyl group) or a pharmaceutically acceptable salt thereof as an active ingredient.

3 Claims, 2 Drawing Sheets

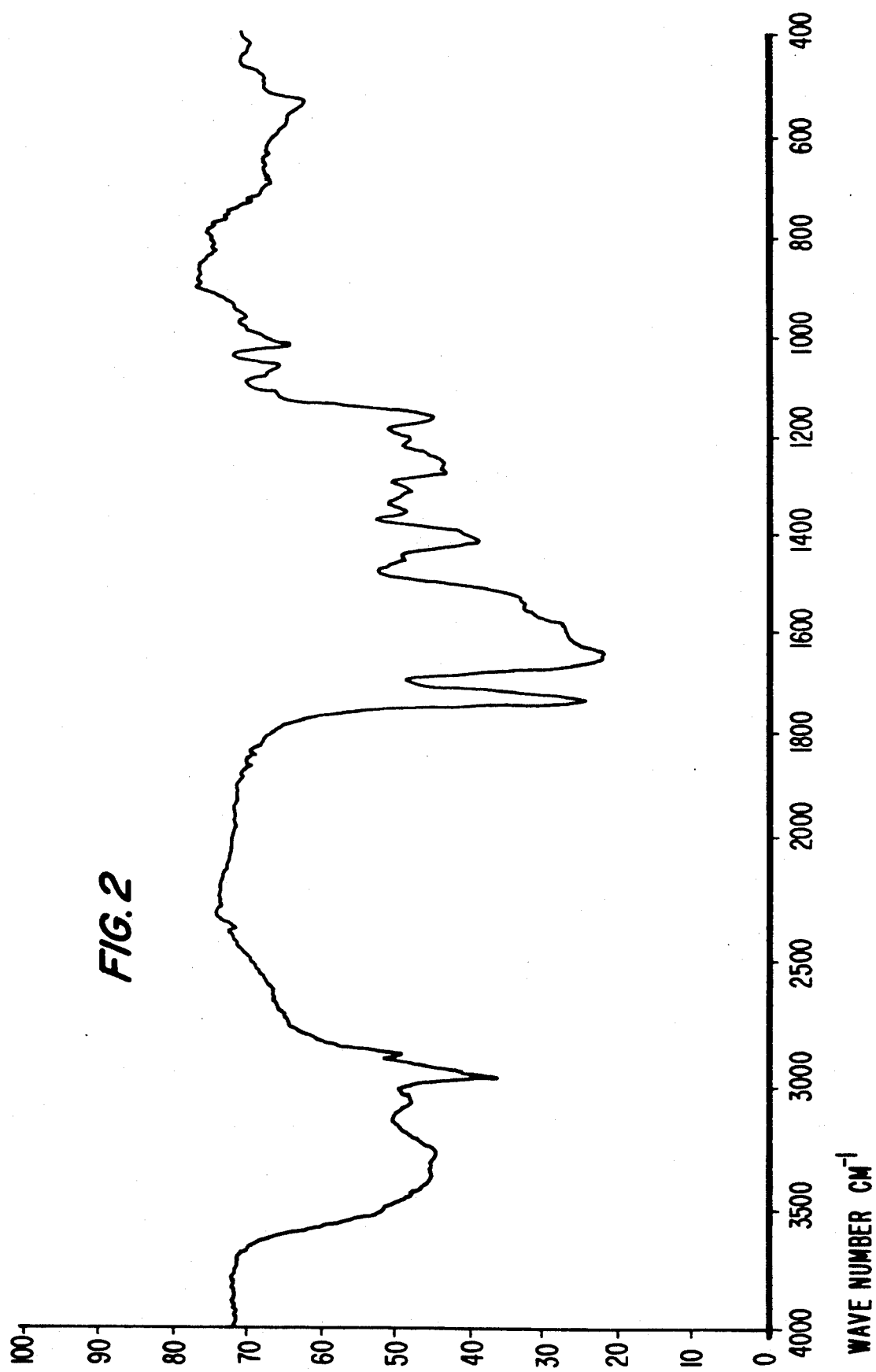

ANTIINFLAMMATORY AND/OR ANTIALLERGIC METHODS

BACKGROUND OF THE INVENTION

1. Field of the Invention

The present invention relates to a useful non-sterodial antiinflammatory and/or antiallergic composition. More particularly, the invention relates to a useful antiinflammatory and/or antiallergic composition containing the substance S-(α,β-dicarboxyethyl)gluthathione which is found in the mammalian body or an ester derivative thereof, or a pharmaceutically acceptable salt thereof as an active ingredient.

2. Description of the Prior Art

There are known a variety of steroidal and nonsteroidal antiinflammatory and/or antiallergic agents. While the steroids have potent antiinflammatory or antiallergic activity, repeated administration of large doses over a long time causes reduced resistance to infection and aggravates diabetes, triggering serious adverse reactions which are life-threatening at times. Therefore, these steroidal antiinflammatory or antiallergic drugs have the disadvantage that, in chronic treatment, the utmost circumspection with constant monitoring of the clinical course is essential.

On the other hand, extensive research is underway for developing nonsteroidal antiinflammatory or antiallergic drugs not conductive to the above-mentioned adverse effects but such nonsteroidal drugs not only tend to induce gastrointestinal and other side effects, such as ulcer, but are inadequate in efficacy as compared with the steroidal counterparts.

In the meantime, the inventors made an extensive exploration into various compounds which would exhibit strong antiinflammatory and antiallergic activities without inducing the above-mentioned side effects and found surprisingly that S-(α,β-dicarboxyethyl)glutathione, which is a substance present in the mammalian body, and some ester derivatives thereof have very strong antiinflammatory and antiallergic activity and can be utilized as drugs with utmost safety. The present invention is predicated on the above findings.

SUMMARY OF THE INVENTION

The present invention is, therefore, directed to an antiinflammatory and/or antiallergic composition characterized by containing a compound of the formula

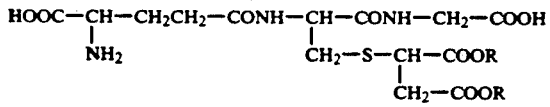

(wherein the R's are the same or different and each means a hydrogen atom or a lower alkyl group) or a pharmaceutically acceptable salt thereof as an active ingredient.

DETAILED DESCRIPTION OF THE INVENTION

S-(α,β-Dicarboxyethyl)glutathione, which is an active ingredient of the pharmaceutical composition of the invention, is a substance present in the animal body which D. H. Calam and S. G. Waley (Biochem. J. 86, 226, 1963) discovered in the bovine crystalline lens but so far its pharmaceutical actions have not been completely elucidated. The present inventors previously discovered that this compound has antihemogglutination activity and platelet aggregation inhibitory activity (Japanese Kokai Patent Publication No. 63-8337/1988 and Japanese Patent Application No. 1-79956/1989).

Referring to the above formula, the R's are the same or different and each means a hydrogen atom or a lower alkyl group. The number of carbon atoms in this lower alkyl group is preferably in the range of 1-10. The carbon chain of this alkyl group may be linear, branched or cyclic, and even be partially cyclic. As such the alkyl group includes methyl, ethyl, n-propyl, i-propyl, n-butyl, t-butyl, sec-butyl, n-pentyl, 1-ethylpropyl, i-pentyl, benzyl and so on.

The compounds of the invention can be used in various applications, as the free acid or as pharmaceutically acceptable salts such as alkali metal salts, e.g. sodium salt, potassium salt, etc., and alkaline earth metal salts, e.g. calcium salt, magnesium salt and so on. The active compound wherein all or part of the carboxyl groups available have formed salts can be used as required in the preparation of the pharmaceutical compositions of the invention.

Depending on the object and necessity, one or more species of the active compounds of the invention can be used in combination.

The active compounds of the invention can be obtained by the following and other methods. Since S-(α,β-dicarboxyethyl)glutathione occurs in yeasts, the bovine lens, etc., it can be extracted and isolated in pure form from such sources by the per se known techniques. Synthetically, S-(α,β-dicarboxyethyl)glutathione can be obtained by allowing equimolar amounts of glutathione and maleic acid to stand in water or aqueous alcohol either at elevated temperature or ambient temperature for 1 to 2 days. Similarly, an ester derivative of S-(α,β-dicarboxyethyl)glutathione can be obtained by using the corresponding monoester or diester of maleic acid. All the compounds thus obtainable contain asymmetrical carbon and, as such, are subject to optical isomerism.

The compounds used as the active ingredient of the pharmaceutical composition of the invention exhibit high antiinflammatory and antiallergic activities at low concentrations as will be apparent from Examples 1- through 3 which appear hereinafter. Further, since the compounds according to the invention are a substance present in the animal body and an ester derivative thereof, they are very low in toxicity and safe as demonstrated in Example 4 presented hereinafter, and can be used advantageously in various dosage forms for the treatment and prevention of various inflammatory or allergic diseases.

The inflammatory diseases which can be treated with this composition include rheumatoid arthritis, spondylosis deformans, osteoarthritis, lumbago, gout attacks, acute otitis media, cystitis, prostatitis, toothache, uvetitis, sinusitis and so on. The composition can also be used advantageously in the treatment of allergic diseases, for example, bronchial asthma, pollinosis, allergic rhinitis dietary allergic gastritis, allergic diarrhea, ulcerative colitis, stomatitis, periarteritis nodosa, obstructive endarteritis, endocarditis, urticaria, eczema, contact dermatitis, phlyctena, sympathetic ophthalmia, allergic conjunctivitis and allergic keratitis.

In the treatment of the above-mentioned inflammatory and allergic diseases, the composition of the invention can be administered orally or otherwise according to the type and mode of diseases. The dosage forms include preparations for external use, such as eye-drops, nasal drops, ear-drops, ointments, creams, poultices, dusting powders, spray mists, liniments and suppositories; oral preparations, such as solutions, powders, capsules, tablets, fine granules and granules, and various injections. These preparations can be manufactured by the established pharmaceutical procedures. These preparations may be made by admixing one or more of the present compounds with the conventional binders, disintegrators, lubricants, thickening agents, resorption-stimulating agents, surfactants, isotonizing agents, stabilizers, preservatives, emulsifiers, pH-adjusting agents and other excipients.

The dosage of the active ingredient is dependent on the patient's age and body weight, dosage form, indications and so on. For example, the adult dosage for injection may range from about 1 to 100 mg/dose once a day and the adult dosage for oral administration is about 10 to 1,000 mg/dose a few times a day. For external use, the drug may be administered in a concentration of about 0.1 to 5 (W/W) % a few times a day as required.

Unless contrary to the objects of the invention, the pharmaceutical composition of the invention may further contain other antiinflammatory and/or antiallergic agents as well as other medicinally effective ingredients.

EXAMPLES

The following examples and pharmaceutical preparation examples are further illustrative of the invention.

EXAMPLE 1

Effect on Rat Carrageenan-Induced Conjunctival Edema

Male Wistar rats weighing about 130 g were used in the experiment. S-($\alpha,\beta$-Dicarboxyethyl)glutathione (hereinafter referred to as DCE-GS) dissolved in physiological saline and adjusted with sodium hydrochloride to pH 7 was administered in doses of 3, 10 and 30 mg/kg to rats through the caudal vein (control group: physiological saline). DCE-GS diethyl ester sodium, DCE-GS monoethyl ester sodium, DCE-GS di-n-butyl ester sodium, and glutathione (hereinafter referred to as GSH) were respectively administered in doses of 30 mg/kg (physiological saline to the control group). One minute later, 50 $\mu$l of 1% carrageenan solution was injected beneath the palpebral conjunctiva of the rat under pentobarbital anesthesia. After three hours, each rat was sacrificed and conjunctival edema was isolated and weighted. Results:

DCE-GS inhibited rat carrageenan-induced conjunctival edema dose-dependently, demonstrating that this substance has high antiinflammatory activity. The other three DCE-GS ester derivatives also significantly inhibited edema weight, attesting to their antiinflammatory activity. In contrast, GSH showed no antiinflammatory effect.

TABLE 1

| Test substance | Dose (mg/kg) | Edema Weight (mg ± S.E.) | % Inhibition |
|---|---|---|---|
| Physiological saline | — | 71.7 ± 3.6 | — |
| DCE-GS | 3 | 50.5 ± 1.9* | 29.6 |
|  | 10 | 44.9 ± 2.4* | 37.4 |

TABLE 1-continued

| Test substance | Dose (mg/kg) | Edema Weight (mg ± S.E.) | % Inhibition |
|---|---|---|---|
|  | 30 | 44.9 ± 2.2* | 37.4 | n = 10, significant difference from physiological saline:
*$p < 0.001$.

TABLE 2

| Test substance | Dose (mg/kg) | Edema weight (mg ± S.E.) | % Inhibition |
|---|---|---|---|
| Physiological saline | — | 73.7 ± 2.9 | — |
| DCE-GS diethyl ester sodium | 30 | 49.7 ± 2.6** | 32.6 |
| DCE-GS monoethyl ester sodium | 30 | 58.5 ± 2.0** | 20.6 |
| DCE-GS di-n-butyl ester sodium | 30 | 60.9 ± 2.8* | 17.4 |
| GSH | 30 | 74.8 ± 3.5 | −1.5 | n = 10, significant difference from physiological saline:
*$p < 0.01$,
**$p < 0.001$.

EXAMPLE 2

Inhibitory Effect on the Release of Histamine from Rat Peritoneal Exudate Cells (1) Preparation of rat peritoneal cell suspension Male SD rats weighing 250 to 280 g were used. The rat peritoneal cells were collected and isolated according to the method of Sullivan et al. First, the rat was bled to death by decapitation and immediately the hair of the abdomen was shaved, the skin was incised a few centimeters, and 10 ml of mast cell medium (MCM) was injected into the peritoneal cavity using a 18-G needle while picking up the muscle with tweezers, followed by 90-sec gentle massage. Then, the abdomen was opened to collect as much ascites as possible using a Terumo syringe. The ascites contaminated with blood was not used in the experiment. The ascites was layered in a polycarbonate tube containing 2 ml of 40% Ficoll 400 (Pharmacia) dissolved in MCM, allowed to stand at room temperature for 30 minutes, and centrifuged at 700 rpm at 4° C. for 10 minutes. Then, the sediment in the upper layer of Ficoll 400 was pipetted and washed three times with about 7 ml of MCM. The cells were counted with a Burker-Turk cytometer and using MCM as a diluent, a cell suspension of about $10^5$ cells/ml (rat peritoneal cell suspension) was prepared. Mast cells were identified by staining intracellular granules with 0.05% toluidine blue.

(2) Release of histamine from mast cells

After 0.8 ml of rat peritoneal cell suspension was preincubated at 37° C. for 10 minutes, 0.1 ml of the test drug was added. The system was incubated for 5 minutes, at the end of which time 0.1 ml of 10 $\mu$g/ml of Compound 48/80 (Sigma) in physiological saline was added. After 10 minutes' incubation, the reaction mixture was cooled in ice-water for 10 minutes to terminate the reaction and centrifuged at 700 rpm at 4° C. for 5 minutes. Then, histamine in the supernatant was determined by HPLC in accordance with the method of Shore et al. as partially modified. Results:

The histamine release rate in the control group was 75.0%. DCE-GS inhibited histamine release concentration-dependently. This demonstrated that DCE-GS has high degranulation-inhibiting activity.

TABLE 3

| Group | Concentration (M) | % Release* | % Inhibition |
|---|---|---|---|
| Control | — | 75.0 ± 6.7 | — |
| DCE-GS | $10^{-3}$ | 2.9 ± 3.4 | 96.1 |
|  | $10^{-4}$ | 59.4 ± 6.2 | 20.8 |
|  | $10^{-5}$ | 73.4 ± 6.5 | 2.1 |

Mean ± S.E. (standard error), n = 3
*The histamine release from a control specimen deproteinized by boiling was taken as 100%.

EXAMPLE 3

Effect on Passive Anaphylaxis of the Back of the Rat

Male Wistar rats weighing about 130 g were used in the experiment. The back hair of each rat was clipped with clippers. The rat antiserum was injected intradermally at the back of the rat. After three days, DCE-GS was administered in doses of 3, 10 and 30 mg/kg (physiological saline to controls) into the caudal vein and after one minute 1 ml of a 50:50 (v/v) mixture of the antigen 1% ovalbumin and 2% Evans blue was administered intravenously to induce passive anaphylaxis. After 30 minutes, the rat was sacrificed and the stained area was determined. The pertinent area was removed and the dye was extracted with 20 ml of formaldehyde for determination. Results:

DCE-GS inhibited both the area of stain and the amount of dye on the rat back dose-dependently. This inhibition of passive anaphylactic reaction demonstrated that DCE-GS has high antiallergic activity.

TABLE 4

| Test substance | Dose (mg/kg) | Area (mm²) | Dye (μg/site) |
|---|---|---|---|
| Physiological saline | — | 926 ± 65 <—> | 767 ± 87 <—> |
| DCE-GS | 3 | 866 ± 195 <6.5>* | 633 ± 111 <17.5> |
|  | 10 | 644 ± 88 <30.5>** | 472 ± 98 <38.5> |
|  | 30 | 489 ± 47 <47.2>*** | 434 ± 77 <43.4>* |

Mean ± S.E. (Standard error),
n = 4 or 5,
< >: Inhibition (%)
Significant differences from physiological saline:
*$p < 0.05$,
**$p < 0.01$,
***$p < 0.001$.

EXAMPLE 4

Intravenous Acute Toxicity Study

The intravenous acute toxicity study of DCE-GS was conducted in male ddY mice, weighing about 20 g, in groups of 5. The doses were 100, 200, 400, 800 and 1,600 mg/kg (common ratio 2). All the injections were adjusted with 1N sodium hydrochloride to pH 7. As a result, Seventy-two-hour observation showed neither death nor abnormal behavior.

EXAMPLE OF SYNTHESIS 1

S-(Diethyl-α,β-dicarboxyethyl)Glutathione sodium

In 150 ml of 30 (v/v) % ethanol are dissolved 9.2 g of glutathione and 5.6 g of diethyl maleate and the solution is adjusted to pH 6 with 2 N-sodium hydroxide. The solution is stirred at 50° C. for about 5 hours, at the end of which time 2 drops of the reaction mixture are taken. To this sample is added one drop of 0.01 N-idione test solution and after confirming the disappearance of iodine color, hydrogen sulfide gas is introduced and the reaction mixture is allowed to stand overnight. The reaction mixture is then concentrated to remove the hydrogen sulfide and the residue is dissolved in 150 ml of water followed by dissolution of 6.6 g of copper acetate (monohydrate), whereupon the copper salt begins to separate out gradually. This precipitate is recovered by filtration, rinsed and suspended in 150 ml of water. Then, hydrogen sulfide gas is introduced under stirring to give copper sulfate. This is filtered off and the filtrate is concentrated and the residue is dissolved in 200 ml of ethanol. This solution is adjusted to pH 6 by gradual addition of sodium hydroxide-ethanol, whereupon white crystals are precipitated. The crystals are recovered by filtration, washed with ethanol, dissolved in water and concentrated as much as possible. To the residue is added ethanol for recrystalization and the precipitated crystals are recovered by filtration and dried. The above procedure gives, 8.5 g of S-(diethyl-α,β-dicarboxyethyl)glutathione sodium. TLC (silica gel) Rf=0.28 (n-butanol-acetic acid-water=4:1:1). The IR spectrum is shown in FIG. 1.

EXAMPLE OF SYNTHESIS 2

S-(di-n-butyl-α,β-dicarboxyethyl)glutathione sodium

In 150 ml of 50 (v/v) % of ethanol are dissolved 9.2 g of glutathione and 7.5 g of di-n-butyl maleate and the reaction is carried out in the same manner as described in Example 1. After removal of the solvent, the residue is dissolved in 150 ml of water followed by addition of 200 ml of 3.3% aqueous copper acetate solution, whereupon the water-insoluble copper salt separates out. This precipitate is recovered by filtration, rinsed, suspended in 300 ml of 50 (v/v) % ethanol, and hydrogen sulfide is bubbled into the solution with stirring to convert it to copper sulfide. This precipitate is filtered off and the filtrate is concentrated to remove the hydrogen sulfide. The residue is re-dissolved in 150 ml of 50 (v/v) % ethanol, adjusted to pH about 6 with 2N-sodium hydroxide, and concentrated. To the concentrate are added ethanol, acetone and isopropyl ether and the resulting white crystals are collected by filtration, washed with acetone and dried. This procedure gives 9.7 g of S-(di-n-butyl-α,β-dicarboxyethyl)glutathione sodium, which is hygroscopic. TLC (Silica gel) Rf=0.40 (n-butanol-acetic acid-water=4:1:1).

EXAMPLE OF SYNTHESIS 3

S-(di-n-butyl-α,β-dicarboxyethyl)glutathione calcium

The reaction procedure of Example of Synthesis 2 is repeated except that calcium carbonate is used in lieu of 2N-sodium hydroxide. To the concentration residue is added acetone to give white crystals which are then recrystallized from ethanol-acetone to recover 7.5 g of S-(di-n-butyl-α,β-dicarboxyethyl)glutathione calcium. The IR spectrum is shown in FIG. 2.

EXAMPLE OF SYNTHESIS 4

S-(monoethyl-α,β-dicarboxyethyl)glutathione sodium

In 150 ml of water are dissolved 9.2 g of glutathione and 4.5 g of monoethyl maleate and the solution is adjusted to pH 6.0 with 2N-sodium hydroxide. After the reaction procedure of Example of Synthesis 1 is repeated, the reaction mixture is concentrated and the white crystals separating out on addition of ethanol are collected by filtration, dissolved in water, concentrated and recrystallized from ethanol. Yield 8.0 g. TLC (Silica gel) Rf=0.17 (n-butanol-acetic acid-water=4:1:1).

PREPARATION EXAMPLE 1

| Tablets for oral administration | |
| --- | --- |
| DCE-GS | 100 mg |
| Lactose | 80 mg |
| Starch | 17 mg |
| Magnesium Stearate | 3 mg |

Using the above ingredient per tablet, oral tablets are manufactured by the established pharmaceutical procedure. If necessary, the tablets may be sugar-coated.

PREPARATION EXAMPLE 2

| Injectable solution | |
| --- | --- |
| DCE-GS | 1 g |
| Glucose | 5 g |
| Sodium carbonate | q.s. |
| Distilled water for injection | 100 ml |

In about 70 ml of distilled water for injection is dissolved 1 g of DCE-GS and the solution is adjusted to pH 6.5 by gradual addition of sodium carbonate. Then, glucose is dissolved and the solution is made up to 100 ml and filtered through a bacterial filter. The filtrate is aseptically filled, in 2 ml portions, into glass ampoules which are then sealed to provide injections.

PREPARATION EXAMPLE 3

| Ointment | |
| --- | --- |
| DCE-GS diethyl ester sodium | 20 g |
| White petrolatum | 250 g |
| Stearyl alcohol | 200 g |
| Propylene glycol | 120 g |
| Polyoxyethylene-hydrogenated castor oil 60 | 40 g |
| Glyceryl monostearate | 10 g |
| Methyl p-hydroxybenzoate | 1 g |
| Propyl p-hydroxybenzoate | 1 g |
| Pure water | q.s. |
| Total | 1000 g |

PREPARATION EXAMPLE 4

| Ophthalmic solution | |
| --- | --- |
| DCE-GS | 1.0 (w/v) % |
| Boric acid | 0.7 (w/v) % |
| Sodium acetate | 0.2 (w/v) % |
| Sodium chloride | 0.5 (w/v) % |
| Methyl p-hydroxybenzoate | 0.02 (w/v) % |
| Chlorobutanol | 0.3 (w/v) % |
| 10 (w/v) % sodium hydroxide | q.s. |
| Sterile purified water | to make 100 ml pH 6.5 |

The above ingredients are mixed and dissolved and, then filtered through a bacterial filter to provide an ophthalmic solution (15 ml per container).

BRIEF DESCRIPTION OF THE DRAWINGS

FIG. 2 is an infrared absorption spectrum of S-(di-n-butyl-$\alpha,\beta$-dicarboxyethyl)glutathione calcium.

Figure 1:
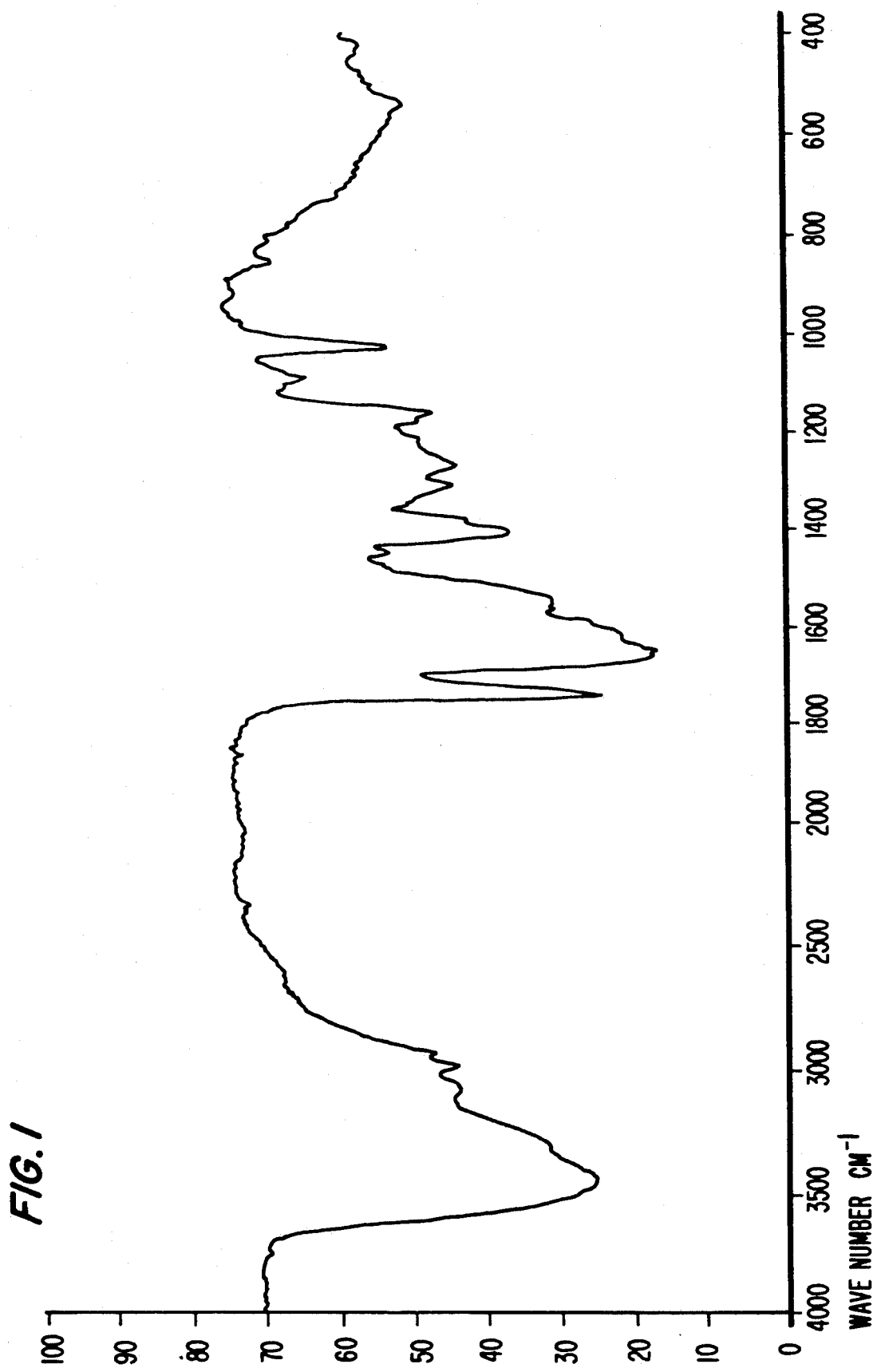
FIG. 1 is an infrared absorption spectrum of S-(diethyl-$\alpha,\beta$-dicarboxyethyl)glutathione sodium.

What is claimed is:

1. A method for the treatment of inflammatory or allergic disease which comprises administering to a patient in need of such treatment an antiinflammatory or antiallergy effective amount of a compound of the formula

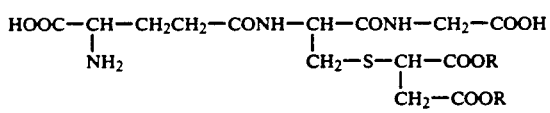

wherein each of the R groups is the same or different and is hydrogen or a lower alkyl group or a pharmaceutically acceptable salt thereof.

2. A method according to claim 1 wherein the inflammatory disease is rheumatoid arthritis, spondylosis deformans, osteoarthritis, lumbago, gout attacks, acute otitis media, cystitis, prostatitis, toothache, uvetitis or sinusitis.

3. A method according to claim 1 wherein the allergic disease is bronchial asthma, pollinosis, allergic rhinitis dietary allergic gastritis allergic diarrhea, ulcerative colitis, stomatitis, periarteritis nodosa, obstructive endarteritis, endocarditis, urticaria, eczema, contact dermatitis, phylctena, sympathetic ophthalmia, allergic conjunctivitis or allergic keratitis.

* * * * *